(12) United States Patent
Gil et al.

(10) Patent No.: US 9,956,144 B2
(45) Date of Patent: May 1, 2018

(54) PROCESS FOR PARTICLE PROCESSING OF ACTIVE PHARMACEUTICAL INGREDIENTS

(75) Inventors: Marco Gil, Odivelas (PT); Constanca Cacela, Rio Maior (PT); Ricardo Mendonca, Feijo (PT); Filipe Gaspar, Oeiras (PT)

(73) Assignee: HOVIONE INTER LIMITED, Lucerne (CH)

( * ) Notice: Subject to any disclaimer, the term of this patent is extended or adjusted under 35 U.S.C. 154(b) by 0 days. days.

(21) Appl. No.: 13/642,397

(22) PCT Filed: Apr. 21, 2011

(86) PCT No.: PCT/GB2011/000631
§ 371 (c)(1),
(2), (4) Date: Dec. 20, 2012

(87) PCT Pub. No.: WO2011/131947
PCT Pub. Date: Oct. 27, 2011

(65) Prior Publication Data
US 2013/0203717 A1 Aug. 8, 2013

(30) Foreign Application Priority Data
Apr. 21, 2010 (PT) ........................................ 105058

(51) Int. Cl.
| | |
|---|---|
| *A61J 3/02* | (2006.01) |
| *A61K 9/00* | (2006.01) |
| *A61K 9/14* | (2006.01) |
| *A61K 31/137* | (2006.01) |
| *A61K 31/46* | (2006.01) |
| *A61K 31/56* | (2006.01) |
| *A61K 31/58* | (2006.01) |

(52) U.S. Cl.
CPC ............... *A61J 3/02* (2013.01); *A61K 9/0075* (2013.01); *A61K 9/14* (2013.01); *A61K 31/137* (2013.01); *A61K 31/46* (2013.01); *A61K 31/56* (2013.01); *A61K 31/58* (2013.01)

(58) Field of Classification Search
CPC ...... A61K 9/0075; A61K 9/14; A61K 31/137; A61K 31/56; A61K 31/58; A61K 31/46; A61J 3/02
See application file for complete search history.

(56) References Cited

U.S. PATENT DOCUMENTS

| | | |
|---|---|---|
| 6,180,781 B1 | 1/2001 | Yuen et al. |
| 6,187,765 B1 | 2/2001 | Harris et al. |
| 6,555,139 B2 * | 4/2003 | Sharma .......................... 424/489 |
| 8,034,381 B2 | 10/2011 | Moschwitzer |
| 2004/0258756 A1 * | 12/2004 | McLoughlin .................. 424/489 |
| 2006/0257335 A1 * | 11/2006 | Southall et al. ................. 424/59 |
| 2007/0178051 A1 | 8/2007 | Pruitt et al. |
| 2008/0226722 A1 * | 9/2008 | Van Tomme ........ A61K 9/0024 514/1.1 |
| 2009/0263333 A1 * | 10/2009 | Lulla et al. ..................... 424/45 |
| 2010/0040691 A1 | 2/2010 | Richards et al. |

FOREIGN PATENT DOCUMENTS

| | | |
|---|---|---|
| EP | 1834624 A1 | 9/2007 |
| EP | 2050437 A1 | 4/2009 |
| JP | 2004137272 A | 5/2004 |
| JP | 2008536812 A | 9/2008 |
| JP | 2009515941 A | 4/2009 |
| WO | 01/32125 A2 | 5/2001 |
| WO | 2005094788 A1 | 10/2005 |
| WO | 2006073154 A1 | 7/2006 |
| WO | 2009017250 A1 | 2/2009 |

OTHER PUBLICATIONS

Huang et al. (J. Microencapsulation, 2003, 20 (4), 459-472).*
Pilcer, G. et al., "Preparation and Characterization of Spray-Dried Tobramycin Powders Containing Nanoparticles for Pulmonary Delivery," International Journal of Pharmaceutics, 2009, pp. 162-169, vol. 365.
PCT International Search Report and Written Opinion, PCT/GB2011/000631 filed Apr. 21, 2011, dated Nov. 23, 2011.
PCT International Preliminary Report on Patentability, PCT/GB2011/000631 filed Apr. 21, 2011, dated Sep. 14, 2012.
Pitchayajittipong, "Engineering of Particles for Inhalation", A thesis submitted for the degree of Doctor of Philosophy, University of Bath, Department of Pharmacy and Pharmacology, 2008, pp. 1-248.
Intellectual Property Office of Singapore Search Report and Written Opinion, Application No. 201207861-4 dated Oct. 7, 2013.
Japanese Office Action, Application No. 2013-505534, dated Aug. 29, 2014.
Japanese Office Action, Application No. JP 2013-505534, dated May 10, 2016.

* cited by examiner

*Primary Examiner* — Johann R Richter
*Assistant Examiner* — Genevieve S Alley
(74) *Attorney, Agent, or Firm* — MacMillan, Sobanski & Todd, LLC

(57) ABSTRACT

A process for reducing the particle size of an active pharmaceutical ingredient (API) while maintaining its polymorphic form, comprises the step of processing the active pharmaceutical ingredient by cavitation at elevated pressure. The process preferably comprises the step of isolating the processed active ingredient in the form of powder, wherein the isolation step comprises filtration or spray drying. Particles produced by the process of the invention typically have a span value of less than 2.5.

24 Claims, 4 Drawing Sheets

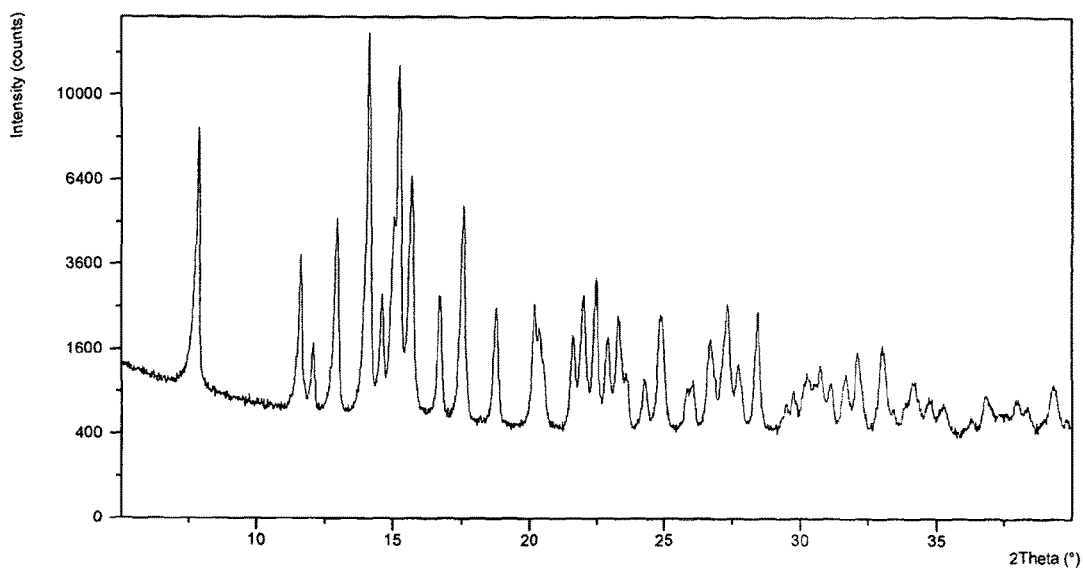
Figure 1 - XRPD diffractogram of Mometasone furoate monohydrate after HPC followed by SD

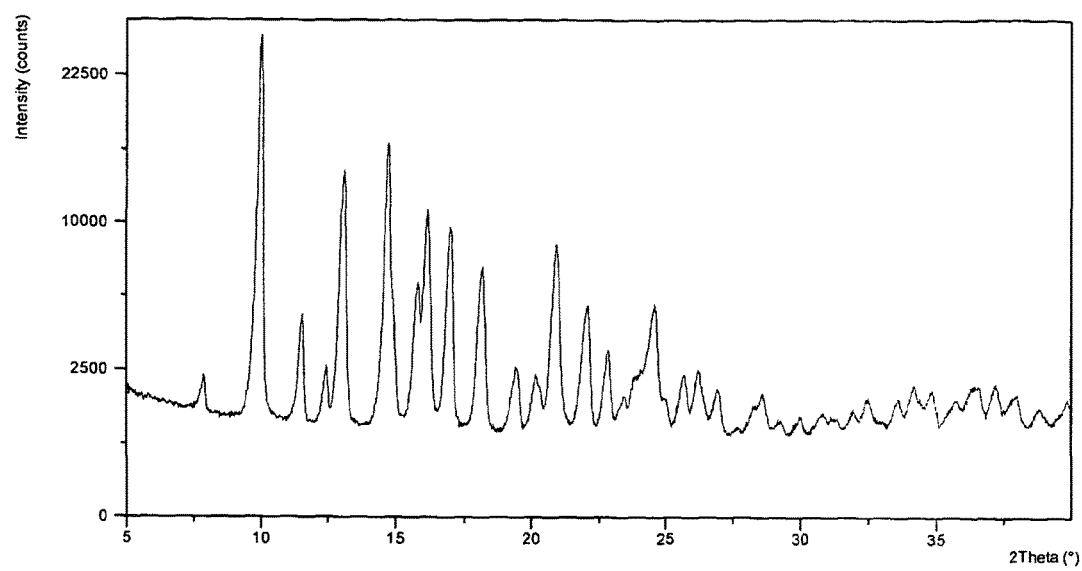
Figure 2 - XRPD diffractogram of Fluticasone propionate after HPC followed by SD.

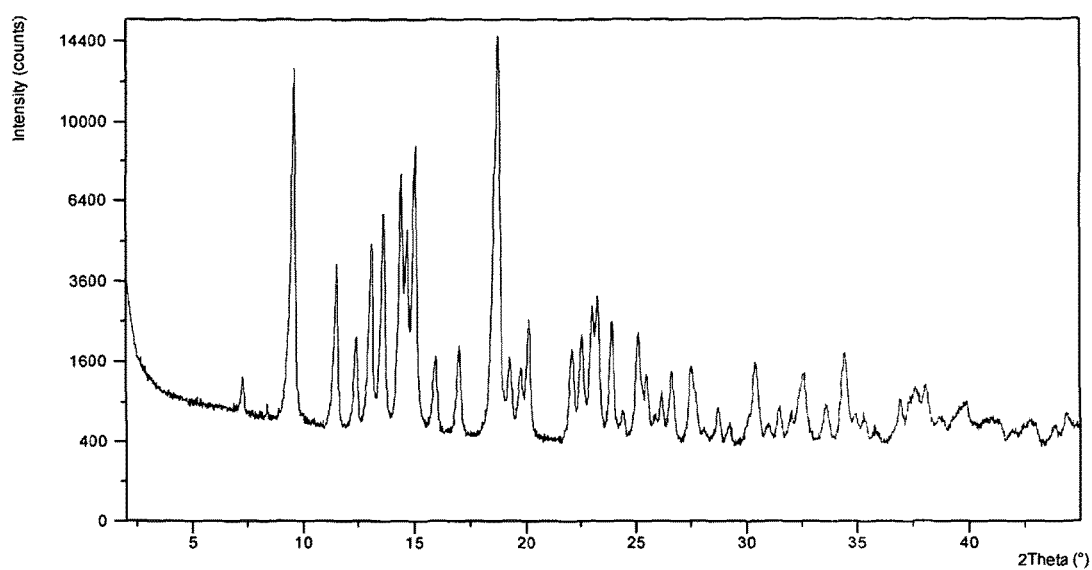
Figure 3 - XRPD diffractogram of Fluticasone furoate after HPC followed by SD.

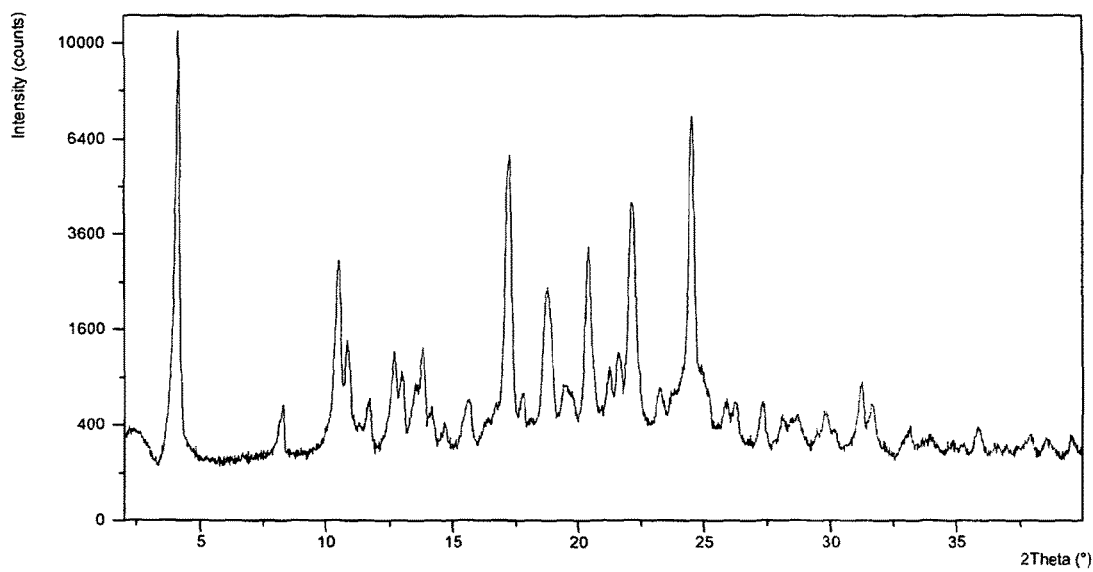
Figure 4 - XRPD diffractogram of salmeterol xinafoate after HPC followed by SD.

PROCESS FOR PARTICLE PROCESSING OF ACTIVE PHARMACEUTICAL INGREDIENTS

The present invention claims the benefit of the PCT/GB2011/000631 filed Apr. 21, 2010, which claims priority to Ser. PT/105058 filed Apr. 21, 2010.

The present invention relates to a process for particle processing and size reduction of active pharmaceutical ingredients. The process comprises wet milling, specifically by cavitation at elevated pressure, and is preferably followed by spray drying. This process enables the control of the particle size and size distribution without altering the polymorphic form of the active pharmaceutical ingredient.

The present invention relates to a new process for particle size reduction of active pharmaceutical ingredients which comprises wet milling, specifically by cavitation at elevated pressure, where the product is preferably suspended in water or other solvent where it is insoluble, and then preferably this is followed by spray drying of the suspension to obtain the product as a dry powder.

According to one aspect of the present invention, there is provided a process for reducing the particle size of an active pharmaceutical ingredient while maintaining its polymorphic form, which process comprises the step of processing the active pharmaceutical ingredient by cavitation at elevated pressure. In a preferred aspect, the processed active ingredient is then spray dried.

The process of the invention is preferably performed on the active pharmaceutical ingredient in isolation, in the absence of any excipients, other than any suspending solvent needed for the processing.

The invention also encompasses an active pharmaceutical ingredient (API) obtainable or obtained by a process according to the process of the invention.

The invention also provides the use of cavitation at elevated pressure to reduce the particle size of an active pharmaceutical ingredient while maintaining its polymorphic form. Preferably the cavitation is followed by isolation of the active by spray drying.

A particular feature of this invention is that the process herein disclosed does not change the crystalline or polymorphic form of the active pharmaceutical ingredient. For example, it is well known that the particle size reduction of some active pharmaceutical ingredients like mometasone furoate monohydrate by traditional methods (e.g: air-jet milling) partially or completely changes the crystalline form to anhydrous (Form I) or the amorphous form of the active ingredient. This invention aims at solving this problem presented by this and other active pharmaceutical ingredients that are subject to changes in their crystalline form when subject to traditional particle reduction methods.

After processing or treatment according to the invention, the particles of API are preferably 95% (by weight) or more, more preferably 99% (by weight) or more, identical with the particles of API prior to processing in terms of the crystalline or polymorphic form of the crystals. If a crystalline starting material is used, preferably 2% (by weight) or less, more preferably 1% (by weight) or less, of the particles after processing comprise amorphous material. In other words, preferably 98% (by weight) or more, more preferably, 99% or more of the particles after processing comprise crystalline material.

Additionally, the invention described herein enables the precise control of particle size reduction with very narrow distributions by tuning operating parameters such as pressure, concentration and number of cycles or recirculation duration. The invention also provides high reproducibility and the isolation of active ingredient as a dry powder. This is an innovative feature offering a substantial advantage over traditional particle size reduction methods, allowing for the isolation of stable active pharmaceutical ingredient particles that can be used in different formulations where particle size is of importance, including but not restricted to powders or suspensions delivered to the airways, injectable suspensions, or formulations for dermatological use.

Another particular feature of this invention is the production of powders characterized by the fact that they present a high fine particle fraction necessary for drug delivery to the respiratory system but without the necessity for stabilizing additives, making this method especially suitable for the manufacture of formulations useful in lung and nasal delivery.

Another aspect of this invention is that the process described herein to micronize and isolate the material in powder form is easily scaled up and can be applied at industrial scale. In particular, the use of high pressure cavitation apparatus (e.g. like those supplied by MFIC or Bee International and spray dryers (e.g like those supplied by Niro) of large scale can be attained as described in this invention.

The particle size reduction of active pharmaceutical ingredients is a key unit operation in the pharmaceutical industry. The ultimate goal of this process is to enhance the deposition of drugs delivered to the lung and to the nose through the optimization of the aerodynamic properties of the drug particles. The most common particle size reduction techniques (e.g: jet milling, ball milling) involve high thermal stresses at the crystal surface that may induce a certain degree of disorder in the crystalline structure producing, in some cases, high levels of amorphous content in the micronized powder or changes in the polymorphic form.

Despite the fact that cavitation at elevated pressures and spray drying are processes relatively well described in the literature for many different applications, they are not described in sequence as a solution for those products which by other particle size reduction processes suffer polymorphic transformation. US patent application US20070178051 describes a process comprising spray drying of a previously processed formulation containing surface stabilizer, for the purpose of better blending of the mixture of the active ingredient-excipient and isolation of stable nanoparticles.

Additionally, for most active pharmaceutical ingredients, the precise control of particle size reduction with very narrow distributions, high reproducibility and the isolation of active ingredient in powder form, presenting high fine particle fractions for lung delivery without stabilizing additives, is yet to be achieved at an industrial scale.

For example, in the case of fluticasone propionate, the particle size reduction process described in the literature is air jet milling. However with this process, the control of the particle size distribution is difficult and the final product presents high levels of amorphous content. This requires aging of the micronized pharmaceutical ingredient to reduce the level of amorphous content, which is a further process step increasing the production cycle time. There is no indication in the prior art that the process herein described can be used to reduce particle size without undesired polymorphic changes.

In the case of mometasone furoate monohydrate, traditional particle size reduction techniques such as air jet milling and ball milling are known to cause the loss of the bonded water producing the anhydrous or even the amorphous forms. U.S. Pat. No. 6,187,765 disclose the use of microfluidization of a suspension of mometasone furoate monohydrate with other excipients to reduce the particle size distribution of the active pharmaceutical ingredient. However, it does not describe any process to obtain micronized mometasone furoate monohydrate in powder form.

BRIEF DESCRIPTION OF THE FIGURES

FIG. 1: XRPD diffractogram of momesatone furoate monohydrate after high pressure cavitation (HPC) followed by spray drying (SD).

FIG. 2: XRPD diffractogram of fluticasone propionate after high pressure cavitation (HPC) followed by spray drying (SD).

FIG. 3: XRPD diffractogram of fluticasone furoate after high pressure cavitation (HPC) followed by spray drying (SD).

FIG. 4: XRPD diffractogram of salmeterol xinafoate after high pressure cavitation (HPC) followed by spray drying (SD).

In a preferred aspect, the present invention provides a process for the particle size reduction of active pharmaceutical ingredients (APIs) which comprises wet milling, specifically cavitation at elevated pressure, where the product is suspended in water or other solvent where it is insoluble, followed by spray drying of the suspension to obtain product in the form of a dry powder.

The compounds can be suspended in any suitable solvent, such as water or any other inorganic or organic solvent, where they are insoluble. The suspension concentration will be typically between 2 and 60% w/v, preferably between 10 and 50% w/v. The limit of concentration to be employed will be limited by the capability of the high pressure cavitation apparatus to process the material.

The particle size reduction is accomplished by cavitation at elevated pressure of the suspended material in a non-solvent. As will be understood by those in this art, the process consists of applying high pressures to the suspension, followed by sudden expansion through a nozzle, thus producing cavitation forces that are strong enough to fracture the particles. Micro-fluidisation is an alternative term sometimes used in this field to describe this process. For the purposes of the present invention, the term "cavitation at elevated pressure" is essentially synonymous with the term micro-fluidisation. An additional feature of some cavitation equipment is the promotion of particle-particle collision through counter-current liquid streams to further decrease the particle size of the suspended material. The pressure applied is defined only by equipment limitations.

By "elevated pressure" it will be understood that suitably the pressure is around 300 bar or above. Typically, the pressure will be in the range 300 to 3100 bar or 300 to 3500 bar, although higher pressures (eg up to 5000 bar or above) can be used if desired, depending upon the limitations set by the equipment.

The suspension may be passed through a high pressure cavitation apparatus several times until the desired particle size and size distribution is achieved. Such "recirculation" is a preferred feature of the invention. The recirculation may, for example, be performed from 2-30 times (or cycles) depending upon the API. Preferred cycle ranges include from 5 to 25 and 15 to 25. Noteworthy, is the tight particle size distribution that this particle size reduction technology offers when compared to other traditional methods of particle size reduction, and that can be particularly suitable for topical drug delivery to the lung or nose. The process enables particles having a low span value to be produced, and suitably the span value is 2.5 or less. More preferably, the span value is 2.0 or less, or 1.8 or less. As will be clear to those in the art, span is defined by the ratio ((Dv90−Dv10)/Dv50), with Dv being the diameter value at which a defined percentage of the particles (eg 10%, 50% or 90% in the equation) have a diameter equal to or less than the Dv value. Drug delivery is achieved by using a device able to deliver a dose of drug comprised of the particles manufactured according to the process of the present invention, and these devices will deliver the dose either under the inspiratory effort of the patient, or via a pressurization of the dose, through the mouth or the nose.

Depending on the pressures being used in the cavitation process the suspension may warm up to temperatures close to the boiling point of the solvent. A cooling system may be installed in the outlet of equipment and back pressure may also be applied to avoid reaching the boiling point of the solvent.

The micronized suspension as described in this invention can then be filtered or preferably fed to a spray dryer given the difficulties of filtering suspensions with such a small particle size, in order to remove the solvent and obtain the product as dry powder. The spray drying process can be carried out using standard operating conditions. Atomization devices such as two-fluid nozzles or pressure nozzles can be used. Drying temperatures which are dependent on the process solvent and residual solvent level target in the final product can be chosen appropriately as well as feed rates.

The process described herein can be accomplished with any suitable kind of standard high pressure cavitation and spray drying equipment available in the market, making it particularly suitable for scale up to industrial manufacturing. Such equipment is well known to the skilled addressee.

In a preferred aspect, the spray drying (SD) step is done immediately following the cavitation step. By "immediately" we mean the spray drying step is performed within 1 hour, preferably within 30 minutes, of the completion of the cavitation step.

Examples of active pharmaceutical ingredients where this process can be applied to prevent polymorphic transformation and attain precise control of particle size include but are not restricted to amorphous, crystalline, hydrated or solvated forms of active pharmaceutical ingredients and pharmaceutical acceptable salts thereof prone to polymorphic transformation when using traditional particle size reduction technologies, such as most corticosteroids and other active pharmaceutical ingredients. Examples of such compounds are: mometasone and esters thereof (e.g. mometasone furoate, mometasone furoate monohydrate), Fluticasone and esters thereof (e.g. fluticasone proprionate, fluticasone furoate), tiotropium (e.g. tiotropium bromide, tiotropium bromide monohydrate), ciclesonide, budesonide, formoterol, salmeterol, salbutamol, beclomethasone and esters thereof (e.g beclomethasone dipropionate), betamethasone and esters thereof (e.g betamethasone acetate), ipratropium, terbutaline, hydrocortisone and esters thereof (e.g. hydrocortisone 17-propionate 21-acetate) or combinations of two or more of these active pharmaceutical ingredients.

As will be clear to the skilled person, APIs made in accordance with the process of the invention may be incorporated into therapeutically useful pharmaceutical compositions which include appropriate excipients where necessary. For example, powder formulations may be produced by blending particles of an API powder produced by the invention with a suitable particulate excipient such as lactose, or any other appropriate excipient (mannitol, glucose, trehalose, etc) for delivery to the lung or nose. The particles of the invention may be also formulated as a suspension for use in a delivery device such as a pressurized canister with a valve-based dose-metering mechanism.

EXAMPLES

The following examples are given as illustrative only and do not restrict the scope of the invention.

Example 1

1) Mometasone furoate monohydrate (130 g) was suspended in water (867 g) and stirred for 30 min to form a uniform suspension and fed to a lab scale high pressure cavitation (HPC) apparatus operating at pressure of 10 kPsi (689 bar) in recirculation mode, i.e. returning the discharge of HPC to the stirred vessel inlet. After the cavitation step the suspension was transferred to a holding vessel to be used in the next step. The HPC apparatus was rinsed with water and the washes added to the main part of the suspension.
2) The suspension was fed to a lab scale spray dryer, while stirring, with a feed rate of 5 ml/min and a drying temperature of 66° C. The product was collected in a glass flask yielding 72 g.
3) The product isolated presented an XRPD FIG. 1.1 substantially the same as claimed in U.S. Pat. No. 6,180,781B1. The amorphous content determined by dynamic vapour sorption (DVS) was below 1.1% and the anhydrous form was not detected by near infrared spectroscopy. The TGA value was 3.0%. The particle size distribution of the powder produced was $D_v10=1.91$ μm; $D_v50=3.97$ μm; $D_v90=7.47$ μm; span=1.4. See FIG. 1.

Example 2

1) Fluticasone propionate (30 g) was suspended in water (100 g) and stirred until a uniform suspension was obtained and fed to a lab scale HPC operating at a pressure of 40 kPsi (2758 bar) for 20 cycles. After the cavitation step the suspension was transferred to a holding vessel to be used in the next step. The HPC apparatus was rinsed with water and the rinses added to the main part of the suspension.
2) The suspension was fed to a lab scale spray dryer while stirring with a feed rate of 5 ml/min and a drying temperature of 70° C. The product was collected in a glass flask yielding 21 g.
3) The product isolated presented an XRPD substantially the same as the starting material with a particle size distribution of $D_v10=1.20$ μm; $D_v50=2.45$ μm; $D_v90=4.68$ μm; span=1.4. See FIG. 2.

Example 3

1) Fluticasone furoate (9 g) was suspended in water (100 g) and stirred until a uniform suspension obtained and fed to a lab scale HPC operating at a pressure of 30 kPsi (2068 bar) for 20 cycles. After the cavitation step the suspension was transferred to a holding vessel to be used in the next step. The HPC apparatus was rinsed with water and the rinses added to the main part of the suspension.
2) The suspension was fed to a lab scale spray dryer while stirring with a feed rate of 5 ml/min and a drying temperature of 50° C. The product was collected in a glass flask yielding 6.7 g.
3) The product isolated presented an XRPD substantially the same as the starting material with a particle size distribution of $D_v10=0.89$ μm; $D_v50=1.95$ μm; $D_v90=3.78$ μm; span=1.5. See FIG. 3.

Example 4

1) Salmeterol xinafoate (140 g) was suspended in heptane (1400 g) and stirred until a uniform suspension was obtained. Then it was fed to a lab scale HPC operating at a pressure of 15 kPsi (1034 bar) for 7 cycles. After the cavitation step the suspension was transferred to a holding vessel to be used with heptane and the rinses added to the main part of the suspension.
2) The suspension was fed to a lab scale spray dryer while stirring with a feed rate between 12 ml/min and 17 ml/min, drying temperature of 40° C. The product was collected in a glass flask yielding 104 g.
3) The product isolated presented an XRPD substantially the same as the starting material with a particle size distribution of $D_v10=0.33$ μm; $D_v50=1.37$ μm; $D_v90=3.09$ μm; span=2.0. See FIG. 4.

Example 5

1) Tiotropium bromide (20 g) was suspended in acetone (200 g) and stirred until a uniform suspension was obtained. Then it was fed to a lab scale HPC operating at a pressure of 20 kPsi (1379 bar) for 21 cycles. After the cavitation step the suspension was transferred to a holding vessel.
2) The suspension was fed to a lab scale spray dryer while stirring with a feed rate between 6 ml/min, drying temperature of 45° C. The product was collected in a glass flask yielding 13 g.
3) The product isolated presented a particle size distribution of $D_v10=0.74$ μm; $D_v50=2.90$ μm; $D_v90=5.58$ μm; span=1.7.

The invention claimed is:

1. A process for micronizing particles of an active pharmaceutical ingredient (API) while maintaining its polymorphic form, which process comprises the steps of:
   suspending the API at a concentration between 2 and 60% w/v in a solvent in which it is insoluble to produce a suspension;
   processing the suspension of the active pharmaceutical ingredient by cavitation at a pressure in the range of 300 to 3500 bar with a high pressure cavitation apparatus;
   rinsing the high pressure cavitation apparatus with the solvent to produce a wash;
   adding the wash to the suspension; and
   subjecting the suspension to an isolation step to produce a processed active pharmaceutical ingredient in the form of powder;
   wherein the process is performed on the active pharmaceutical ingredient in the absence of any excipients other than the suspending solvent, the resulting particle size distribution of the processed active pharmaceutical ingredient comprises a span ((Dv90−Dv10)/Dv50) of less than 2.5, and the processed active pharmaceutical ingredient comprises microparticles suitable for topical delivery to the lungs or nose.
2. The process according to claim 1 wherein the solvent is water, heptane, an alcohol, a ketone or an alkane, or a mixture of two or more of the above.

3. The process according to claim 1 wherein the isolation step comprises filtration or spray drying.

4. The process according to claim 3, wherein the isolation step comprises spray drying and wherein the spray drying step is done immediately following the cavitation step.

5. The process according to claim 4, wherein the spray drying is conducted within 1 hour of the cavitation step.

6. The process according to claim 1 wherein the active ingredient is mometasone, fluticasone, tiotropium, ciclesonide, budesonide, formoterol, salmeterol, salbutamol, beclomethasone, betamethasone, ipratropium, terbutaline, or hydrocortisone, or a pharmaceutically acceptable salt or ester of one of the above, or a combination of two or more of the above active pharmaceutical ingredients or their pharmaceutically acceptable salts or esters.

7. The process according to claim 6 wherein the active ingredient is mometasone furoate or mometasone furoate monohydrate; fluticasone proprionate or fluticasone furoate; tiotropium bromide or tiotropium bromide monohydrate; ciclesonide; budesonide; formoterol; salmeterol; salbutamol; beclomethasone dipropionate; betamethasone acetate; ipratropium; terbutaline; or hydrocortisone 17-propionate 21-acetate, or a combination of two or more of these active pharmaceutical ingredients.

8. The process according to claim 1 wherein the active ingredient is mometasone furoate monohydrate, fluticasone propionate, fluticasone furoate, salmeterol xinafoate or tiotropium bromide.

9. The process according to claim 8, wherein the solvent is water.

10. The process according to claim 8, wherein the active ingredient is salmeterol xinafoate, and the solvent is heptane.

11. The process according to claim 8, wherein the active ingredient is tiotropium bromide, and the solvent is acetone.

12. The process according to claim 1 wherein the span is less than 2.0.

13. The process according to claim 12 wherein the span is less than 1.8.

14. The process for making a pharmaceutical composition which comprises carrying out a process according to claim 1, and then combining the active pharmaceutical ingredient with one or more pharmaceutically acceptable excipients.

15. The process according to claim 14 wherein the pharmaceutical composition is a powder suitable for topical delivery to the nose or lung.

16. The process according to claim 1, further comprising a step of recirculating the suspension through the high pressure cavitation apparatus one or more times prior to rinsing the high pressure cavitation apparatus with the solvent.

17. The process according to claim 1, wherein the API is suspended at a concentration between 10 and 50% w/v in the solvent.

18. The process according to claim 1, wherein the API is suspended at a concentration between 9 and 30% w/v in the solvent.

19. The process according to claim 1 wherein the API prone to polymorphic transformation is mometasone furoate and the solvent is water.

20. The process according to claim 1 wherein the API prone to polymorphic transformation is fluticasone propionate and the solvent is water.

21. The process according to claim 1 wherein the API prone to polymorphic transformation is fluticasone furoate and the solvent is water.

22. The process according to claim 1 wherein the API prone to polymorphic transformation is salmeterol xinafoate and the solvent is heptane.

23. A process according to claim 1 wherein the API prone to polymorphic transformation is tiotropium bromide and the solvent is acetone.

24. A process for micronizing particles of an active pharmaceutical ingredient (API) while maintaining its polymorphic form, which process comprises the steps of:
   suspending the API at a concentration between 2 and 60% w/v in a solvent in which it is insoluble to produce a suspension;
   processing the suspension of the active pharmaceutical ingredient by cavitation at a pressure in the range of 300 to 3500 bar with a high pressure cavitation apparatus; and
   subjecting the suspension to an isolation step to produce a processed active pharmaceutical ingredient in the form of powder;
   wherein the process is performed on the active pharmaceutical ingredient in the absence of any excipients other than the suspending solvent, the resulting particle size distribution of the processed active pharmaceutical ingredient comprises a span ((Dv90−Dv10)/Dv50) of less than 2.5, and the processed active pharmaceutical ingredient comprises microparticles suitable for topical delivery to the lungs or nose.

* * * * *